United States Patent [19]

Vecchietti et al.

[11] Patent Number: 4,826,819

[45] Date of Patent: May 2, 1989

[54] PIPERIDINE ANALGESICS

[75] Inventors: Vittorio Vecchietti; Massimo Signorini; Antonio Giordani, all of Milan, Italy

[73] Assignee: Dr. Lo Zambeletti S.p.A., Italy

[21] Appl. No.: 91,275

[22] Filed: Aug. 31, 1987

[30] Foreign Application Priority Data

Sep. 2, 1986 [GB] United Kingdom ............... 8621134
Dec. 11, 1986 [GB] United Kingdom ............... 8629642

[51] Int. Cl.$^4$ .................. A61K 31/55; A61K 31/445; C07D 401/06; C07D 211/26
[52] U.S. Cl. .................................. 514/212; 514/316; 514/318; 514/326; 514/331; 540/597; 546/189; 546/208; 546/246
[58] Field of Search ............ 546/189, 208, 246; 540/597; 514/212, 316, 318, 326, 331

[56] References Cited

U.S. PATENT DOCUMENTS 4,753,952 6/1988 Vecchietti et al. ................ 540/597

FOREIGN PATENT DOCUMENTS 52311 5/1982 European Pat. Off. ............ 546/208

OTHER PUBLICATIONS

Chemical Abstracts, vol. 49 (1955), col. 11025 Abstracting U.S. Pat. No. 2,684,965 (to Weston et al.) (assigned to Abbott Labs).
Chemical Abstracts, vol. 91, 1979, 91:103654z.

*Primary Examiner*—Robert T. Bond
*Attorney, Agent, or Firm*—Jacobs & Jacobs

[57] ABSTRACT

A compound of formula (I):

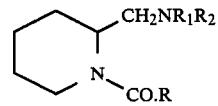

or a salt or solvate thereof in which R.CO is an acyl group in which R is of formula (II)

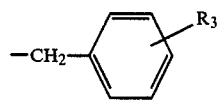

in which $R_3$ is Br, $NO_2$ or $CF_3$; and, $R_1$ and $R_2$ are independently $C_{1-6}$ alkyl or together form a $C_{3-6}$ polymethylene or alkylene group, is useful for treating pain.

9 Claims, No Drawings

PIPERIDINE ANALGESICS

This invention is concerned with novel piperidine derivatives, processes for their preparation, and their use in medicine, particularly as analgesics.

Compounds which are K-receptor agonists act as analgesics through interaction with Kappa opioid receptors. The advantage of K-receptor agonists over the classical $\mu$-receptor agonists, such as morphine, lies in their ability of causing analgesia while being devoid of morphine-like behavioural effects and addiction liability.

European Patent Application No. 86309874.5 discloses a group of azacyclic derivatives which exhibit K-receptor agonism without the behavioural effects of morphine and morphine analogues. A small class of azacyclic derivatives within the scope of the above European Application, but not specifically disclosed therein, has now been discovered, the compounds having improved K-receptor agonism properties which make them potentially useful as analgesics.

According to the present invention there is provided a compound, or a solvate or salt thereof, of formula (I):

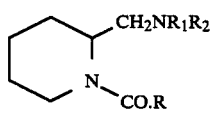

in which: RCO is an acyl group in which R is of the formula (II)

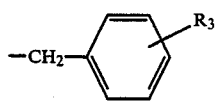

in which
$R_3$ is Br, $NO_2$ or $CF_3$;
and $R_1$ and $R_2$ are independently $C_{1-6}$ alkyl groups or together form a $C_{3-6}$ polymethylene or alkenylene group.

As an alkyl group, each of $R_1$, and $R_2$ may be a methyl, ethyl, propyl, butyl, pentyl or hexyl group, typically methyl.

As a polymethylene group, $R_1$ and $R_2$ together may be propylene, butylene, pentylene or hexylene, typically butylene. As an alkenylene group, $R_1$ and $R_2$ together may be $-CH_2-CH=CH-CH_2-$.

The substituents $R_3$ are preferably at the meta or para positions of the phenyl ring.

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% or 98% or more of the compound of formula I or its salt or solvate.

One preferred pharmaceutically acceptable form is the crystalline form, including such form in a pharmaceutical composition.

Examples of a pharmaceutically acceptable salt of a compound of formula I include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

Examples of a pharmaceutically acceptable solvate of a compound of formula I include the hydrate.

The compounds of formula I have at least one asymmetric centre and therefore exist in more than one stereoisomeric form. The invention extends to all such forms and to mixtures thereof, including racemates. The preferred stereo isomeric form is the (S)-enantiomer.

Specific examples of the invention are:
(2R,S)-1-(3-nitrophenylacetyl)-2-(1-pyrrolidinylmethyl) piperidine hydrochloride;
(2R,S)-1-(3-trifluoromethylphenylacetyl)-2-(1-pyrrolidinylmethyl)piperidine hydrochloride hemihydrate
(2S)-1-(4-trifluoromethylphenylacetyl)-2-(1-pyrrolidinylmethyl) piperidine hydrochloride sesquihydrate;
(2R,S)-1-(4-nitrophenylacetyl)-2-(1-pyrrolidinylmethyl)piperidine hydrochloride;
(2R,S)-1-(4-trifluoromethylphenylacetyl)-2(1-pyrrolidinylmethyl)piperidine hydrochloride;
(2R,S)-1-(4-bromophenylacetyl)-2-(1-pyrrolidinylmethyl)piperidine hydrochloride;
(2R,S)-1-(3-nitrophenylacetyl)-2-dimethylaminomethyl piperidine hydrochloride;
(2R,S)-1-(3-trifluoromethylphenylacetyl)-2-dimethylaminomethyl piperidine hydrochloride.

The present invention also provide a process for the preparation of a compound of formula I which comprises reacting a compound of formula III

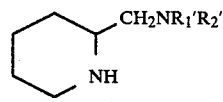

in which
$R_1'$, and $R_2'$, and $R_1$ and $R_2$ as defined for formula I or a group or atom convertible to $R_1$ and $R_2$, with a compound of formula R'CO.OH or an active derivative thereof,
in which
R' is R as defined for formula I or a group convertible to R, to form a compound of formula Ia

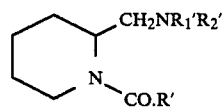

and then performing one or more of the following steps:
(a) where R', $R_1'$ or $R_2'$, are other than R, $R_1$ and $R_2$, converting R', $R_1'$, or $R_2'$ to R, $R_1$ or $R_2$ to obtain a compound of formula I,
(b) where R', $R_1'$ and $R_2'$, are R, $R_1$ and $R_2$, converting one R, $R_1$ or $R_2$ to another R, $R_1$ or $R_2$ to obtain a compound of formula I, (c) forming a salt and/or solvate of the obtained compound of formula I.

Suitable active derivatives of R'CO.OH are acid chlorides or acid anhydrides. Another suitable derivative is a mixed anhydride formed between the acid and an alkyl chloroformate.

For example, in standard methods well known to those skilled in the art, the compound of formula III may be coupled:

(a) with an acid chloride in the presence of an inorganic or organic base,
(b) with the acid in the presence of dicyclohexyl carbodiimide, N-dimethylaminopropyl-N'-ethyl carbodiimide or carbonyl diimidazole,
(c) with a mixed anhydride generated in situ from the acid and an alkyl (for example ethyl)chloroformate.

It will be appreciated that a compound of formula Ia may be converted to a compound of formula I, or one compound of formula I may be converted to another compound of formula I, by interconversion of suitable substituents. Thus certain compounds of formula I and Ia are useful intermediates in forming other compounds of the present invention.

$R_1'$ and $R_2'$ may be alkyl or acyl groups and converted to $R_1'/R_2'$ hydrogen atoms by conventional amine dealkylation or deacylation. When $R_1'$ or $R_2'$ is benzyl or substituted benzyl it may be converted to an $R_1$ or $R_2'$ hydrogen atom by catalytic hydrogenation or other method of reduction. $R_1'$ and $R_2'$ as hydrogen atoms may be converted to $R_1$ and $R_2$ alkyl groups by conventional amine alkylation, or by acylation followed by reduction. $R_1'$ and $R_2'$ are preferably $R_1$ and $R_2$ respectively.

The compound R'CO.OH is of the formula IIa

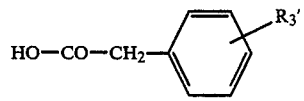

in which $R_3'$ is $R_3$ is as defined for formula II or a group or atom convertible to $R_3$.

Conversions of substituents $R_3'$ on the aromatic group Ar to obtain $R_3$ are generally known in the art of aromatic chemistry. $R_3'$ is preferably $R_3$.

The compounds of formula I may be converted into their pharmaceutically acceptable acid addition salts by reaction with the appropriate organic or mineral acids.

Solvates of the compounds of formula I may be formed by crystallization or recrystallization from the appropriate solvent. For example hydrates may be formed by crystallization or recrystallization from aqueous solutions, or solutions in organic solvents containing water.

Also salts or solvates of the compounds of formula I which are not pharmaceutically acceptable may be useful as intermediates in the production of pharmaceutically acceptable salts or solvates. Accordingly such salts or solvates also form part of this invention.

The compounds of formula I exist in more than one stereoisomeric form and the processes of the invention produces mixtures thereof. The individual isomers may be separated one from another by resolution using an optically active acid such as tartaric acid. Alternatively, an asymmetric synthesis would offer a route to the individual form.

The compound of formula III may be prepared from pipecolinic acid of formula IV by the reaction scheme shown:

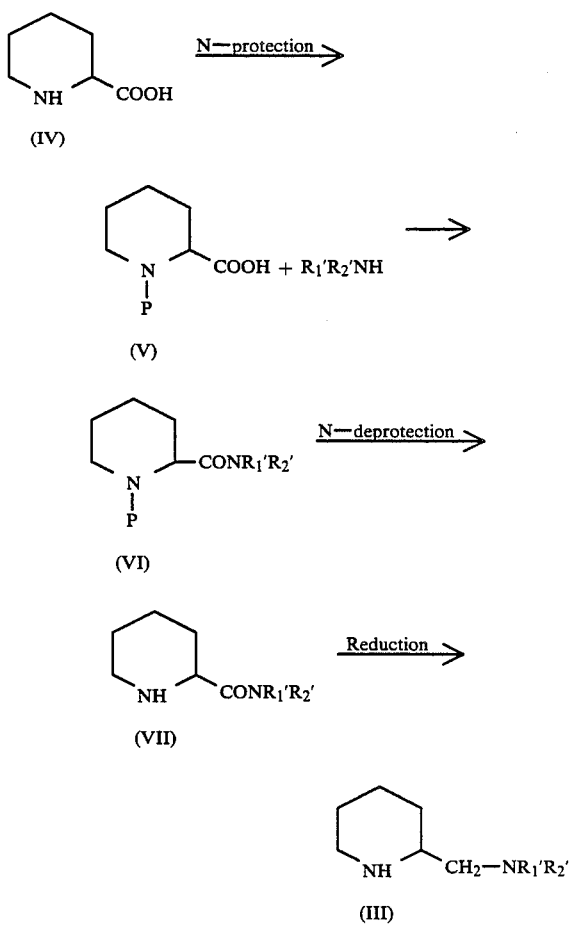

In this scheme, firstly the compound of formula IV is nitrogen protected with a conventional protecting group P, such as benzyloxycarbonyl or tert-butyloxycarbonyl, forming the compound of formula V which is reacted with the amine $R_1'R_2'NH$ (in which $R_1'$ and $R_2'$ are as defined earlier) to obtain N-protected amide VI. This is conventionally N-deprotected, for example by catalytic debenzylation if P is benzyloxycarbonyl or by acid treatment if P is tert-butyloxycarbonyl, and the resulting basic amide VII is reduced to the diamine III by reaction with lithium aluminium hydride.

Alternatively, the N-protected acid V is reduced to a primary alcohol which is esterified, for example with methane sulfonic acid or p-toluenesulfonic acid, and the ester reacted with $R_1'R_2'NH$. Deprotection of the ring nitrogen gives the diamine III.

When the starting material of formula IV is a racemic mixture, the resulting compounds of formulae III and I are also racemic. Using a compound of formula IV in the R- or S-configuration results in the corresponding optically active products.

Pipecolinic acid of formula IV is known compound which is available commercially.

Certain of the intermediates described above are novel compounds and, together with the described processes for their preparation, they form a further aspect of this invention.

The activity of the compounds of formula I in standard analgesic tests indicates that they are of therapeutic utility in the treatment of pain.

Accordingly the present invention also provides a compound of formula I, or a pharmaceutically acceptable salt or solvate thereof, for use as an active therapeutic substance.

The present invention further provides a pharmaceutical composition comprising a compound of formula I, or a pharmaceutically acceptable salt or solvate thereof, and a pharmaceutically acceptable carrier.

The present invention also provides the use of a compound of formula I, or a pharmaceutically acceptable salt or solvate thereof, in the manufacture of a medicament for the treatment of pain.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

The present invention also provides a method of treating pain in mammals, particularly in humans, which comprises administering an effective amount of a compound, pharmaceutically acceptable salt or solvate, or composition of the invention to a sufferer.

The following Examples illustrate the preparation of compounds of the invention.

EXAMPLE 1

(2R,S)-1-(3-nitrophenylacetyl)-2-(1-Pyrrolidinylmethyl) piperidine hydrochloride 1 g. of (2R,S)-2-(1-pyrrolidinylmethyl) piperidine (6 mmoles) and 1.05 g. of 3-nitrophenylacetic acid (6 mmoles) were dissolved in 50 ml of methylene dichloride, the solution cooled to 0° C. and 1.46 g. of dicyclohexylcarbodiimide (0.7 mmoles), dissolved in 10 ml of methylene dichloride were slowly dropped in. After 24 hours at room temperature, the precipitated dicyclohexylurea was filtered off and the solution evaporated to dryness i.v.. The oily residue was taken up in 50 ml of 5% ethanolic hydrogen chloride, and the solution refluxed for one hour. After filtering off an additional amount of dicyclohexylurea, the solution was evaporated to dryness i.v., and the residue partitioned between ether and 15% aqueous sodium hydroxide. The ethereal solution was evaporated to dryness i.v., and the oily residue (2.6 g.) chromatographed on 15 g. of silica gel 60, eluting by methylene dichloride containing increasing amounts of methanol (0 to 1.5%). The oily substance obtained by evaporating to dryness the combined positive fractions was dissolved in ether, a little amount of insoluble material filtered off, and the solution again evaporated to dryness. The residue was dissolved in acetone and the solution cautiously brought to acidic pH by adding ethanolic hydrogen chloride. The precipitate was collected by filtration and crystallized from ethanol.

Yield 0.5 grams
MP 223°–5° C.
$C_{18}H_{25}NO_3O_3HCl0.5H_2O$
M.W. 376.87
Elemental analysis: Calcd. C, 57.36; H, 7.22; N, 11.15; Cl, 9.64; Found C, 57.65; H, 7.13; N, 11.17 Cl, 9.24.
I.R. (KBr) cm$^{-1}$: 1630; 1525; 1345; 1245.
N.M.R. (CDCl$_3$)δ: 1.2–2.45 m (10H); δ: 2.45–3.10 m (3H); δ: 3.3–4.2 m (5H); δ: 4.1 AB system (2H); δ: 5.2 AB system (1H); δ: 7.30–8.20 m (3H).

EXAMPLE 2

(2R,S)-1-(3-trifluoromethylphenylacetyl)-2-(1-pyrrolidinylmethyl)piperidine hydrochloride hemihydrate 1 g. of (2-R,S)-2-(1-pyrrolidinylmethyl) piperidine (6 mmoles) and 1.35 g. of 3-trifluoromethylphenylacetic acid (6.6 mmoles) were dissolved in 30 ml of methylene dichloride, the solution cooled to 0° C. and 1.45 g. of dicyclohexylcarbodiimide, dissolved in 20 ml of methylene dichloride dropped in. After 48 hours standing at room temperature the reaction mixture was evaporated to dryness i.v., and the residue partitioned between 10% aqueous citric acid and ethyl acetate.

Insoluble dicyclohexylurea was filtered off, the organic layer separated and the aqueous layer extracted again with ethyl acetate.

The acidic aqueous layer was made alkaline with 10% aqueous sodium hydroxide, the precipitated oil was extracted with ethyl acetate and the organic phase evaporated to dryness i.v.. The crude oily product was purified by silica gel 60 column chromatography, eluting with methylene dichloride.

The purified base was dissolved in acetone. On cautiously acidifying the solution with ethanolic hydrogen chloride, the hydrochloride precipitated and was collected by suction filtration.

Yield 1 g.
M.P. 186°–8° C.
$C_{19}H_{25}F_3N_2O.HCl.0.5H_2O$
M.W. 399.877
Elemental analysis: Calcd. C, 57.06; H, 6.81; N, 7.00; Cl, 8.87; Found C, 57.55; H, 6.95; N, 6.99; Cl, 8.76.
I.R. (KBr) cm$^{-1}$: 1655; 1450; 1335; 1245.

N.M.R. (CDCl$_3$) δ: 1.2–2.5 m (10 H); δ: 2.5–3.1 m (3H); δ: 3.2–4.2 m (5H); δ: 4.1 AB system (2 H); δ: 5.2 m (1 H); δ: 7.3–7.8 m (3 H).

EXAMPLE 3

(2S)-1-(4-trifluoromethylphenylacetyl)-2-(1-pyrrolidinylmethyl)-piperidine hydrochloride sesquihydrate 400 mg of (2S)-2-(1-pyrrolidinylmethyl) piperidine (2.38 mmoles) and 500 mg of 4-trifluoromethylphenylacetic acid (2.5 mmoles) were dissolved in 30 ml of methylene dichloride. Into this solution, held at 0° C., 0.54 mg of dicyclohexylcarbodiimide, dissolved in 10 ml of methylene dichloride, were slowly dropped.

After 24 hours standing at 0° C., the reaction mixture was worked up as described in Example 2 yielding an oily product, which was transformed into the hydrochloride by dissolving in acetone and cautiously acidifying to pH2 by means of ethanolic hydrogen chloride.

Yield 0.53 g.
M.P. 87°–8° C.
[α] D$^{20}$= −39.6 (C=1, MeOH)
$C_{19}H_{25}F_3N_2O$. HCl 1.5H$_2$O
M.W. 417.895
Elemental analysis: Calcd. C, 58.38; H, 6.71; N, 7.17; Cl. 9.07; F, 14.58; Found C, 58.30; H, 6.74; N, 7.11; Cl, 9.11; F, 14.58.
I.R. (KBr) cm$^{-1}$: 1630; 1335; 1120;
N.M.R. (CDCl$_3$) δ: 1.2–2.4 m (10 H); δ: 2.4–3.1 m (3H); δ: 3.3–4.2 m (5H); δ: 4.1 AB system (2 H); J AB=15.8 Hz δ: 5.22 dd (1 H); J'=12.3 Hz, J''=3.22 Hz δ: 7.5 AB system (4 H).

Intermediate (i)

(S)-N-benzyloxycarbonyl pipecolinic acid

This was prepared by a standard method from (S)-pipecolinic acid (15 g., 0.116 moles) and benzylchloroformate (19.25 ml, 0.135 moles) in 2N aqueous sodium hydroxide.
Yield 19.1 g.
M.P. 119°–20° C. (from diisopropylether)

Intermediate (ii)

(2S)-N-benzyloxycarbonyl-2-(1-pyrrolidinylcarbonyl) piperidine

This was prepared from 8.6 g. (0.0326 moles) of Intermediate (i), via the mixed anhydride with isobutylchloroformate and subsequent reaction with a slight excess of pyrrolidine.
Yield 9.8 g.
Oil

Intermediate (iii)

(2S)-2-(1-pyrrolidinylcarbonyl) piperidine

Intermediate (ii) was hydrogenated in a Parr apparatus, in 120 ml of 90% acetic acid, in the presence of 1 g. of 10% Pd on carbon.
Yield 5.5 g.
Oil
The hydrochloride melts at 249°–50° C.

Intermediate (iv)

(2S)-2-(1-pyrrolidinylmethyl) piperidine 5.3 g. of Intermediate (iii) (0.029 moles), dissolved in 30 ml. THF, were dropped into a suspension of 2 g. of LiAlH$_4$ (0.052 moles) in 20 ml. of THF, held at room temperature. After 12 hours standing at room temperature and 3 hours at 40°–45° C., the reaction mixture was worked up by the standard procedure.

Yield 4.1 g.

B.p. 110°–12° C./20 mm Hg

EXAMPLE 4

(2R,S)-1-(4-nitrophenylacetyl)-2-(1-pyrrolidinylmethyl)piperidine hydrochloride 3 g of (2R,S)-2-(1-pyrrolidinylmethyl)piperidine (18 mmoles) and 4 g. of 4-nitrophenylacetic acid (22 mmoles) were dissolved in 70 ml of methylene dichloride, the solution cooled to −10° C. and 7.4 g of dicyclohexyldicarbodiimide dissolved in 70 ml of methylene dichloride dropped in.

After 24 hours at room temperature the precipitated dicyclohexylurea was filtered off and the solution evaporated to dryness i.v.. The oily residue was taken up in 50 ml of 5% ethanolic hydrogen chloride, and the solution warmed at 40° C. for 30 minutes.

After filtering off any additional dicyclohexylurea, the solution was evaporated to dryness i.v., and the residue partitioned between ether and 15% aqueous sodium hydroxide. The ethereal solution was evaporated to dryness i.v., and the oily residue (4.8 g.) chromatographed on 30 g of silica gel 60, eluting by methylene dichloride containing increasing amounts of methanol (0 to 1.5%). The oily substance obtained by evaporating to dryness the combined positive fractions was dissolved in ether, refluxed with charcoal for 5 minutes, filtered, and the solution again evaporated to dryness. The residue was dissolved in acetone and the solution cautiously brought to acidic pH by adding methanolic hydrogen chloride. The precipitate was collected by filtration and crystallized from ethanol.

Yield 1.2 grams

M.P. 195°–97° C.

$C_{18}H_{26}N_3O_3Cl$

M.W. 376.869

Anal.calcd.for $C_{18}H_{26}N_3O_3Cl$: C: 58.76; H: 7.12; N: 11.42; Cl: 9.65 found: C: 58.65; H: 7.09; N: 11.36; Cl: 9.63.

IR (KBr): 1640 cm$^{-1}$ $H^1$ N.M.R. (CDCl$_3$): 1.2–3.1δ,m (14H); 3.3–4.2δ,m(4H); 4.2δ; AB system, J=15 Hz (2H); 5.25δ,m (1H);

7.96δ, AB system, J=9 Hz (4H).

EXAMPLE 5

(2R,S)-1-(4-trifluoronethylphenylacetyl)-2-(1pyrrolidinylmethyl)piperidine hydrochloride 0.8 g. of (2R,S)-2-(1-pyrrolidinylmethyl)piperidine (5 mmoles) and 1.6 g. of 4-trifluoromethylphenylacetic acid (7.8 mmoles) were dissolved in 20 ml of methylene dichloride, the solution cooled to 0° C. and 3 g of dicyclohexylcarbodiimide, dissolved in 20 ml of methylene dichloride dropped in.

After 48 hours standing at room temperature the reaction mixture was evaporated to dryness i.v., and the residue partitioned between 10% aqueous citric acid and ethyl acetate.

Insoluble dicyclohexylurea was filtered off, the organic layer separated and the aqueous layer extracted again with ethyl acetate.

The acid aqueous layer was made alkaline with 10% aqueous sodium hydroxide, the precipitated oil was extracted with ethyl acetate and the organic phase evaporated to dryness i.v..

The crude oily product was purified by silica gel 60 column chromatography, eluting by methylene dichloride containing increasing amounts of methanol (0 to 1.5%). The purified base was dissolved in acetone. On cautiously acidifying the solution with ethanolic hydrogen chloride, the precipitated hydrochloride was collected by suction filtration.

Yield 1.3 grams

M.P. 180°–84° C.

$C_{19}H_{26}N_2OF_3Cl$

M.W. 390.871

IR (KBr): 1635 cm$^{-1}$ $H^1$N.M.R. (CDCl$_3$): 1.2–2.35 δ, m (12H); 2.6–3.2 δ, m (2H); 3.2–4.2 δ, m (4H); 4.1 δ, AB system (2H); 7.55 δ, AB system (4H).

EXAMPLE 6

(2R,S)-1-(4-bromophenylacetyl)-2-(1-pyrrolidinylmethyl)piperidine hydrochloride 1.2 g of (2R,S)-(1-pyrrolidinylmethyl)piperidine (7 mmoles) and 1.6 g. of 4-bromophenylacetic acid (10 mmoles) were dissolved in 30 ml of methylene dichloride, the solution cooled to 0° C. and 3.7 g of dicyclohexylcarbodiimide (18 mmoles), dissolved in 30 ml of methylene dichloride were slowly dropped in.

After 28 hours at room temperature the dicyclohexylurea was filtered off and the solution evaporated to dryness i.v..

The oily residue was taken up 80 ml of 5% ethanolic hydrogen chloride, and the solution was warmed at 40° C. for one hour.

After filtering off any additional dicyclohexylurea, the solution was evaporated to dryness i.v., and the residue partitioned between ether and 15% aqueous sodium hydroxide.

The ethereal solution was evaporated to dryness i.v., and the oily residue (2.8 g.) chromatographed on 30 g. of silica gel 60, eluting by methylene dichloride containing increasing amounts of methanol (0 to 1.2%). The combined positive fractions were evaporated to dryness i.v., and the oily residue was dissolved in ether, and brought to acid pH by adding ethanolic hydrogen chloride.

The precipitate was collected by filtration and crystallized from ethanol.

Yield 1.3 grams

M.P. 197°–9° C.

$C_{18}H_{26}N_2OBrCl$

M.W. 401.777

Anal.calcd.for $C_{18}H_{26}N_2OBrCl$: C: 53.80; H: 6.52; N: 6.97; Cl: 8.83; Br: 19.89 found: C: 53.69; H: 6.55; N: 6.94; Cl: 8.87 Br: 19.79

IR (KBr): 1645 cm$^{-1}$ $H^1$ N.M.R. (CDCl$_3$): 1.3–1.8 δ, m (6H); 1.8–2.5 δ, m (4H); 2.5–3.0 δ, m (4H); 3.2–4.2 δ, m (4H); 3.9 δ, AB system (2H), 5.25 δ, m (1H); 7.3 δ, AB system (4H).

EXAMPLE 7

(2R,S)-1-(3-nitrophenylacetyl)-2-dimethylaminomethyl piperidine hydrochloride 1.5 g of (2R,S)-(1-dimethylaminomethyl piperidine (10 mmoles) and 3.2 g of 3-nitrophenylacetic acid (18 mmoles) were dissolved in 35 ml of dry methylene dichloride, the solution cooled to −10° C. and 4 g of dicyclohexylcarbodiimide dissolved in 35 ml of methylene dichloride dropped in.

After 12 hours at room temperature the precipitated dicyclohexylurea was filtered off and the solution evaporated to dryness i.v..

The residue was partitioned between 10% aqueous citric acid and ethyl acetate.

Insoluble dicyclohexylurea was filtered off, the organic layer separated and the aqueous layer extracted again with ethyl acetate.

The acidic aqueous layer was made alkaline with 10% aqueous sodium hydroxide, the precipitated oil was extracted with ethyl acetate and evaporated to dryness i.v..

The oily product was purified by silica gel 60 column chromatography, eluting by methylene dichloride containing increasing amounts of methanol (0 to 1.5%).

The purified base was dissolved in acetone; the hydrochloride was precipitated by acidifying with ethanolic hydrogen chloride, and collected by suction filtration.

Yield 0.6 grams
M.P. 200°-202° C.
$C_{16}H_{24}N_3O_3Cl$
M.W. 341.833
IR (KBr): 1650 cm$^{-1}$

EXAMPLE 8

(2R,S)-1-(3-trifluoromethylphenylacetyl)-2-dimethylaminomethyl piperidine hydrochloride 1.5 g of (2R,S)-2-dimethylaminomethyl piperidine (10 mmoles) and 2.2 g of 3-trifluoromethylphenylacetic acid (10 mmoles) were dissolved in 40 ml of dry methylene dichloride, the solution cooled to −10° C. and 4 g of dicyclohexylcarbodiimide dissolved in 40 ml of methylene dichloride dropped in.

After 12 hours at room temperature the precipitated dicyclohexylurea was filtered off and the solution evaporated to dryness i.v..

The residue was partitioned between 10% aqueous citric acid and ethyl acetate.

Insoluble dicyclohexylurea was filtered off, the organic layer separated and the aqueous layer extracted again with ethyl acetate.

The acidic aqueous layer was made alkaline with 10% aqueous sodium hydroxide, the precipitated oil was extracted with ethyl acetate and evaporated to dryness i.v..

The oily product was purified by silica gel 60 column chromatography, eluting by methylene dichloride containing increasing amounts of methanol (0 to 1.5%). The purified base was dissolved in acetone; the hydrochloride was precipitated by acidifying with ethanolic hydrogen chloride, and collected by suction filtration.

Yield 0.5 grams
M.P. 168°-170° C.
$C_{17}H_{24}N_3OF_3Cl$
M.W. 364.835
IR (KBr) : 1640 cm$^{-1}$ Examples 1 to 8 are summarised in the following Table:

TABLE I

General Formula: piperidine with CH$_2$-N(R$_1$)(R$_2$)·HX substituent and N-COR

| Example No. | R | R$_1$, R$_2$ | Salt | Molecular Formula | Molecular Weight | Melting Point (0° C.) |
|---|---|---|---|---|---|---|
| 1 | −CH$_2$−(3-NO$_2$-phenyl) | −(CH$_2$)$_4$− | HCl·0.5H$_2$O | $C_{18}H_{27}N_3O_{3.5}Cl$ | 376.87 | 223–25 |
| 2 | −CH$_2$−(3-CF$_3$-phenyl) | −(CH$_2$)$_4$− | HCl·0.5H$_2$O | $C_{19}H_{27}N_2O_{1.5}ClF_3$ | 399.879 | 186–88 |
| 3 | −CH$_2$−(4-CF$_3$-phenyl) (S) isomer | −(CH$_2$)$_4$− | HCl·1.5H$_2$O | $C_{19}H_{29}N_2O_{2.5}ClF_3$ | 417.895 | 87–88 |
| 4 | −CH$_2$−(4-NO$_2$-phenyl) | −(CH$_2$)$_4$− | HCl | $C_{18}H_{26}N_3O_3Cl$ | 367.869 | 195–97 |
| 5 | −CH$_2$−(4-CF$_3$-phenyl) | −(CH$_2$)$_4$− | HCl | $C_{19}H_{26}N_2OClF_3$ | 390.871 | 180–84 |

TABLE I-continued

General Formula: cyclohexane ring with N-COR substituent and CH$_2$-N(R$_1$)(R$_2$)·HX side chain

| Example No. | R | R$_1$, R$_2$ | Salt | Molecular Formula | Molecular Weight | Melting Point (0° C.) |
|---|---|---|---|---|---|---|
| 6 | —CH$_2$—C$_6$H$_4$—Br | —(CH$_2$)$_4$— | HCl | C$_{18}$H$_{26}$N$_2$OBrCl | 401.777 | 197–99 |
| 7 | —CH$_2$—C$_6$H$_4$—NO$_2$ | R$_1$ = R$_2$ = CH$_3$ | HCl | C$_{16}$H$_{24}$N$_3$O$_3$Cl | 341.833 | 200–02 |
| 8 | —CH$_2$—C$_6$H$_4$—CF$_3$ | R$_1$ = R$_2$ = CH$_3$ | HCl | C$_{17}$H$_{24}$N$_2$OClF$_3$ | 364.835 | 168–70 |

The pharmacological activity of compounds of this invention is illustrated by in vitro and in vivo methods, using the following test procedures. The test results are summarised in Table II.

Pharmacological Test Methods

Mouse Tail-flick test (Modified from the procedure published by D'Amour et al., J. Pharm. Exptl. Ther. 72, 74/1941)

Male Charles River mice, average weight 26 g, are used. Selection is carried out before beginning of experiments: only mice whose reaction time is less than 8 sec. are used. They are randomly distributed into groups of 10 and dosed with compounds under test, with positive and negative controls being included.

Compounds under test are administered subcutaneously in isotonic saline in a volume of 20 ml.Kg$^{-1}$. 30 min later, mice are placed again under heat source (Socrel apparatus) and reaction time is recorded.

Analgesic activity of the test compound is expressed as the percent number of mice doubling the initial time within a group.

$$\% \text{ analgesia} = \frac{\text{No. of mice doubling the reaction time}}{\text{Total no. of mice per group}} \times 100$$

RECEPTOR AFFINITY STUDY

Tissue preparation

Radio receptor binding to $\mu$ and k sites is performed on fresh guinea pig brain homogenate prepared according to Kosterlitz. (1981).

Whole brain without cerebellum is homogenized in 50 mM, Tris-buffer (pH 7.4 at 0° C.) and centrifuged at 49,000×g×10 min. The pellet is then resuspended in the same buffer, incubated at 37° C. for 45 min. and centrifuged again.

1.9 ml of the final homogenate (1:100 in Tris-pH 7.4, 0° C.) is used for the binding assay.

Binding to $\mu$ sites (Magnan J., 1982)

$^3$H [D-Ala$^2$, MePhe$^4$, Gly-ol$^5$] Enkephalin ($^3$H-DAGO), an enkephalin analogue that binds selectively to $\mu$-receptors, is added to the biological substrate and incubated at 25° C. for 40 min., filtered through Whatman GF-C and washed with ice-cold Tris-buffer.

The filters are then dried, solubilized in Filtercount and the radioactivity monitored. Non specific binding is determined in the presence of 10$^{-6}$M Naloxone.

Binding to K sites (Magnan J., 1982)

The binding of tritiated Ethylketocyclazocine to brain homogenate is measured in the presence of 100 nanomolar D-Ala-D-LeuEnkephalin (DADLE) and 100 nanomolar DAGO, added to saturate the $\delta$ and $\mu$ opioid receptors respectively.

Final homogenate with solutions of the cold ligand and of the labelled ligand is incubated for 40 min at 25° C., filtered through Whatman GF/C glass filter discs and washed.

The radioactivity bound to the filters is counted by liquid scintillation spectrophotometry.

MR 2266,500 nM is utilized to determine the saturable binding.

For the calculation of the kinetic parameters of the binding of labelled and unlabelled ligands, the equilibrium dissociation constant (K$_D$), and the inhibition constant (Ki) and the maximum number of binding sites (B max) are determined from saturation curves and competition experiments (Hill 1910; Scatchard 1949; Cheng and Prusoff 1973; Gillan et al. 1980).

A concentration of radioligand near K$_D$ is used in the binding assays evaluating our compounds.

Hill, A.V. (1910): J.Physiol.40. IV-VIII (1910)
Scatchard G. (1949): Ann.N.Y.Acad.Sci.,51,660–674
Cheng and Prusoff W. H.: Biochem.Pharmac.22,30-99–3102, (1973)
Gillan M. G. C.,Kosterlitz: Br.J.Pharmac. 70, 481–490, H. W. and Paterson S. Y. (1980)
Kosterlitz H. W.,: Br.J.Pharmac. 73, 939–949, Paterson S. Y. and Robson (1981) L. E.

Magnan J., Paterson: Arch. Pharmacol. 319, S. Y., Tavani A., and 197–205, (1982) Kosterlitz H. W.

TABLE II
TEST RESULTS

| Example Nos. | MOUSE TAIL-FLICK | | | OPIATE RECEPTOR BINDING Ki(nM) | |
|---|---|---|---|---|---|
| | SUBCUTANEOUS | | ORAL | | |
| | % Protection 1 mg Kg$^{-1}$ | ED$_{50}$ mg Kg$^{-1}$ | ED$_{50}$ mg/Kg os | μ | K |
| 1 | | 0.97 | 4.61 | >10,000 | 5.96 |
| 2 | | 0.43 | 4.61 | >10,000 | 3.07 |
| 3 | | 0.14 | 0.67 | 2535 | 4.05 |
| 4 | 80 | 0.55 | 5.45 | 12,830 | 37.90 |
| 5 | 100 | 0.23 | 1.08 | 3091 | 3.59 |
| 6 | 80 | 0.52 | 4.12 | 3130 | 6.61 |

We claim:

1. A compound of formula (I):

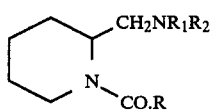

or a salt or solvate thereof in which
R.CO is an acyl group in which R is of formula (II)

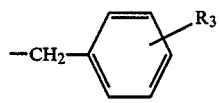

in which
R$_3$ is Br, NO$_2$ or CF$_3$;
and, R$_1$ and R$_2$ are independently C$_{1-6}$ alkyl or together form a C$_{3-6}$ polymethylene or alkylene group.

2. A compound according to claim 1, in which each of R$_1$ and R$_2$ is methyl, ethyl, propyl, butyl, pentyl or hexyl.

3. A compound according to claim 1, in which R$_1$ and R$_2$ together form a propylene, butylene, pentylene or hexylene group, or a —CH$_2$—CH=CH—CH$_2$— group.

4. A compound according to claim 1 in which R$_3$ is at the meta- or para-position on the phenyl ring.

5. A compound according to claim 1 in the form of an (S)-enantiomer.

6. A compound selected from:
(2R,S)-1-(3-nitrophenylacetyl)-2-(1-pyrrolidinylmethyl)piperidine hydrochloride;
(2R,S)-1-(3-trifluoromethylphenylacetyl)-2-(1-pyrrolidinylmethyl)piperidine hydrochloride hemihydrate;
(2S)-1-(4-trifluoromethylohenylacetyl)-2-(1-pyrrolidinylmethyl)piperidine hydrochloride sesquihydrate;
(2R,S)-1-(4-nitrophenylacetyl)-2-(1-pyrrolidinylmethyl)piperidine hydrochloride;
(2R,S)-1-(4-trifluoromethylphenylacetyl)-2-(1-pyrrolidinylmethyl)piperidine hydrochloride;
(2R,S)-1-(4-bromophenylacetyl)-2-(1-pyrrolidinylmethyl)piperidine hydrochloride;
(2R,S)-1-(3-nitrophenylacetyl)-2-dimethylaminomethyl piperidine hydrochloride;
(2R,S)-1-(3-trifluoromethylphenylacetyl)-2-dimethylamino-methyl piperidine hydrochloride.

7. A pharmaceutical composition comprising a compound according to claim 1, and a pharmaceutically acceptable carrier.

8. A composition according to claim 7 in unit dosage form.

9. A method of treating pain in mammals which comprises administering an effective, non-toxic amount of a compound according to claim 1 to a sufferer.

* * * * *

UNITED STATES PATENT AND TRADEMARK OFFICE
CERTIFICATE OF CORRECTION

PATENT NO. : 4,826,819
DATED : May 2, 1989
INVENTOR(S) : VITTORIO VECCHIETTI ET AL

It is certified that error appears in the above-identified patent and that said Letters Patent is hereby corrected as shown below:

In the Abstract set forth on the title page, last line, change "alkylene" to --alkenylene--.

Claim 1, line 2 from below, change "alkylene" to --alkenylene--.

Signed and Sealed this

Sixth Day of February, 1990

Attest:

JEFFREY M. SAMUELS

Attesting Officer     Acting Commissioner of Patents and Trademarks